United States Patent
Ebbett et al.

(10) Patent No.: US 9,232,990 B2
(45) Date of Patent: Jan. 12, 2016

(54) SKIN GRIPPING MEANS, INJECTOR INCLUDING THE SKIN GRIPPING MEANS AND METHOD OF PERFORMING A SUBCUTANEOUS INJECTION

(75) Inventors: Todd D. Ebbett, Hamilton (NZ); Rodney G. Walker, Hamilton (NZ)

(73) Assignee: Simcro Limited, Hamilton (NZ)

( * ) Notice: Subject to any disclaimer, the term of this patent is extended or adjusted under 35 U.S.C. 154(b) by 185 days.

(21) Appl. No.: 13/322,706

(22) PCT Filed: May 28, 2010

(86) PCT No.: PCT/NZ2010/000098
§ 371 (c)(1),
(2), (4) Date: Feb. 2, 2012

(87) PCT Pub. No.: WO2010/138001
PCT Pub. Date: Dec. 2, 2010

(65) Prior Publication Data
US 2012/0130344 A1      May 24, 2012

(30) Foreign Application Priority Data

May 28, 2009    (NZ) .......................................  577279

(51) Int. Cl.
*A61M 5/42*      (2006.01)
*A61D 7/00*      (2006.01)
(Continued)

(52) U.S. Cl.
CPC .. *A61D 7/00* (2013.01); *A61D 1/00* (2013.01); *A61M 5/3287* (2013.01); *A61M 5/425* (2013.01); *A61M 5/204* (2013.01); *A61M 5/31581* (2013.01); *A61M 5/46* (2013.01)

(58) Field of Classification Search
CPC ...... A61M 37/0069; A61M 5/42; A61M 5/46; A61M 5/158; A61M 5/3287; A61M 25/02; A61M 5/3213; A61M 5/3243; A61D 1/02; A61D 1/025; A61D 1/00; A01K 11/00; A01K 11/005; A01K 11/001; A61B 5/150183
USPC .......................................... 604/115, 174, 506
See application file for complete search history.

(56) References Cited

U.S. PATENT DOCUMENTS 3,324,854  A  *  6/1967  Weese ................... A61M 5/425
                                                   604/115
5,017,007  A  *  5/1991  Milne .................. G01N 21/658
                                                   356/301

(Continued)

FOREIGN PATENT DOCUMENTS

NZ             515487        1/2004
WO   WO 2004069301 A2 *    8/2004    .......... A61M 5/3129

*Primary Examiner* — Bhisma Mehta
*Assistant Examiner* — Jenna Zhang
(74) *Attorney, Agent, or Firm* — Dykema Gossett PLLC

(57) ABSTRACT

A skin gripping means for use with an injector (200) is disclosed. In one embodiment the skin gripping means is a needle guard (100). An exterior surface (7) of the skin gripping means (100) is provided with a plurality of fingers (6) adapted to engage a subject's skin (9) when in use. A method of performing a subcutaneous injection is also disclosed with includes the steps of bringing a skin gripping means (100) of an injector (200) into contact with the skin (9) of a subject, moving the skin gripping means (100) substantially parallel to the skin (9) to thereby form a fold (10) in the skin, moving a needle (11) of the injector (200) into the fold (10) to a suitable position for a subcutaneous injection and injecting a substance through the needle (11).

8 Claims, 7 Drawing Sheets

(51) Int. Cl.
  *A61D 1/00* (2006.01)
  *A61M 5/32* (2006.01)
  *A61M 5/46* (2006.01)
  *A61M 5/20* (2006.01)
  *A61M 5/315* (2006.01)

(56) References Cited

U.S. PATENT DOCUMENTS

| | | | |
|---|---|---|---|
| 5,364,362 A * | 11/1994 | Schulz | A61D 1/025 |
| | | | 604/115 |
| 5,609,577 A | 3/1997 | Haber et al. | |
| 5,634,906 A | 6/1997 | Haber et al. | |
| 6,066,116 A | 5/2000 | Fox | |
| 2004/0138622 A1* | 7/2004 | Palasis | A61B 17/3207 |
| | | | 604/173 |
| 2005/0209566 A1* | 9/2005 | Yeshurun et al. | 604/173 |
| 2006/0129123 A1* | 6/2006 | Wojcik | A61M 5/158 |
| | | | 604/506 |
| 2006/0287664 A1* | 12/2006 | Grage, Jr. | A61B 5/1411 |
| | | | 606/181 |
| 2007/0232999 A1 | 10/2007 | Perez | |
| 2008/0015624 A1* | 1/2008 | Sonoda | A61M 5/158 |
| | | | 606/185 |
| 2008/0018123 A1* | 1/2008 | Cox | A61F 13/10 |
| | | | 294/25 |
| 2009/0012494 A1* | 1/2009 | Yeshurun | A61M 37/0015 |
| | | | 604/506 |
| 2010/0137831 A1* | 6/2010 | Tsals | A61M 5/3243 |
| | | | 604/506 |
| 2010/0145283 A1 | 6/2010 | Walker et al. | |

\* cited by examiner

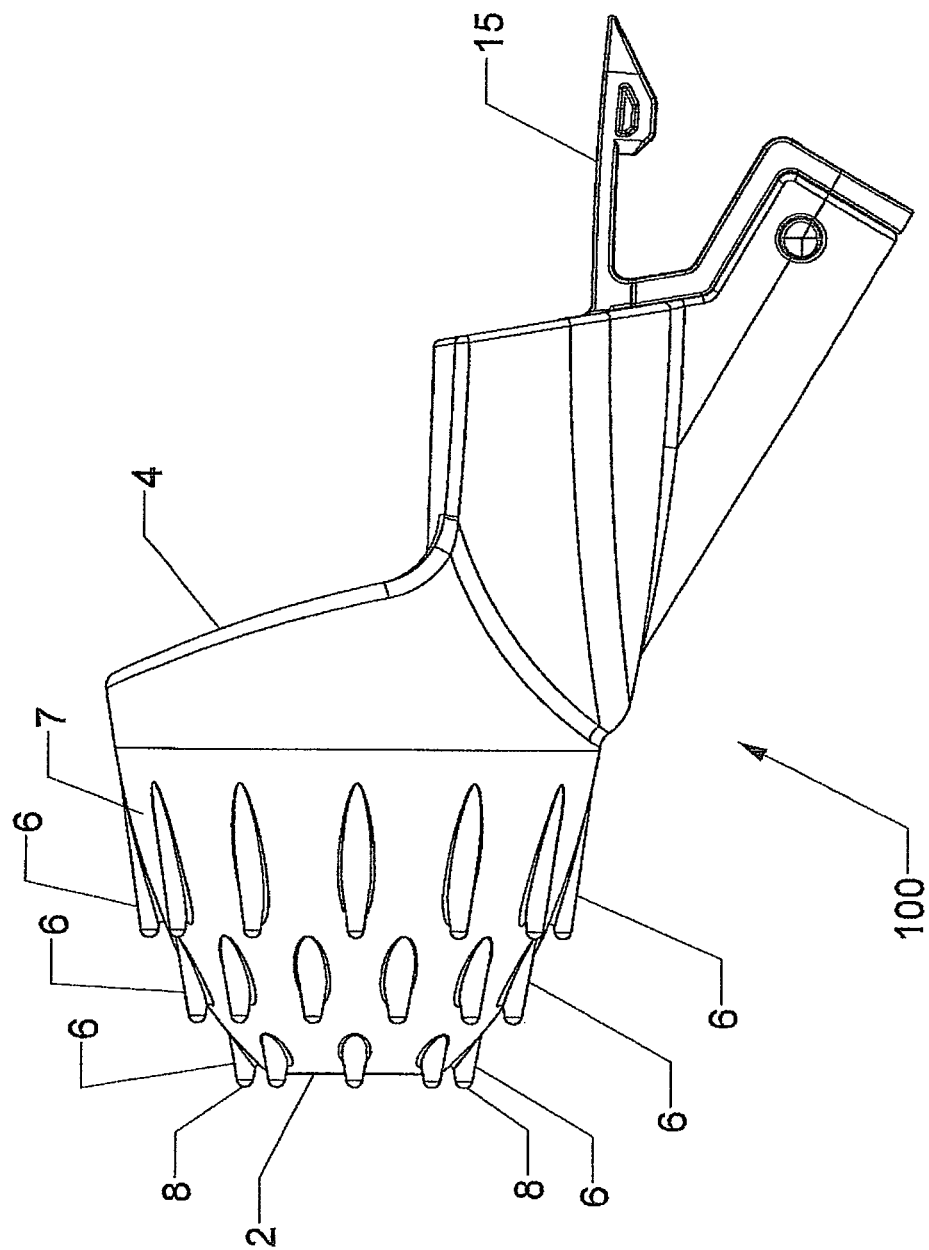

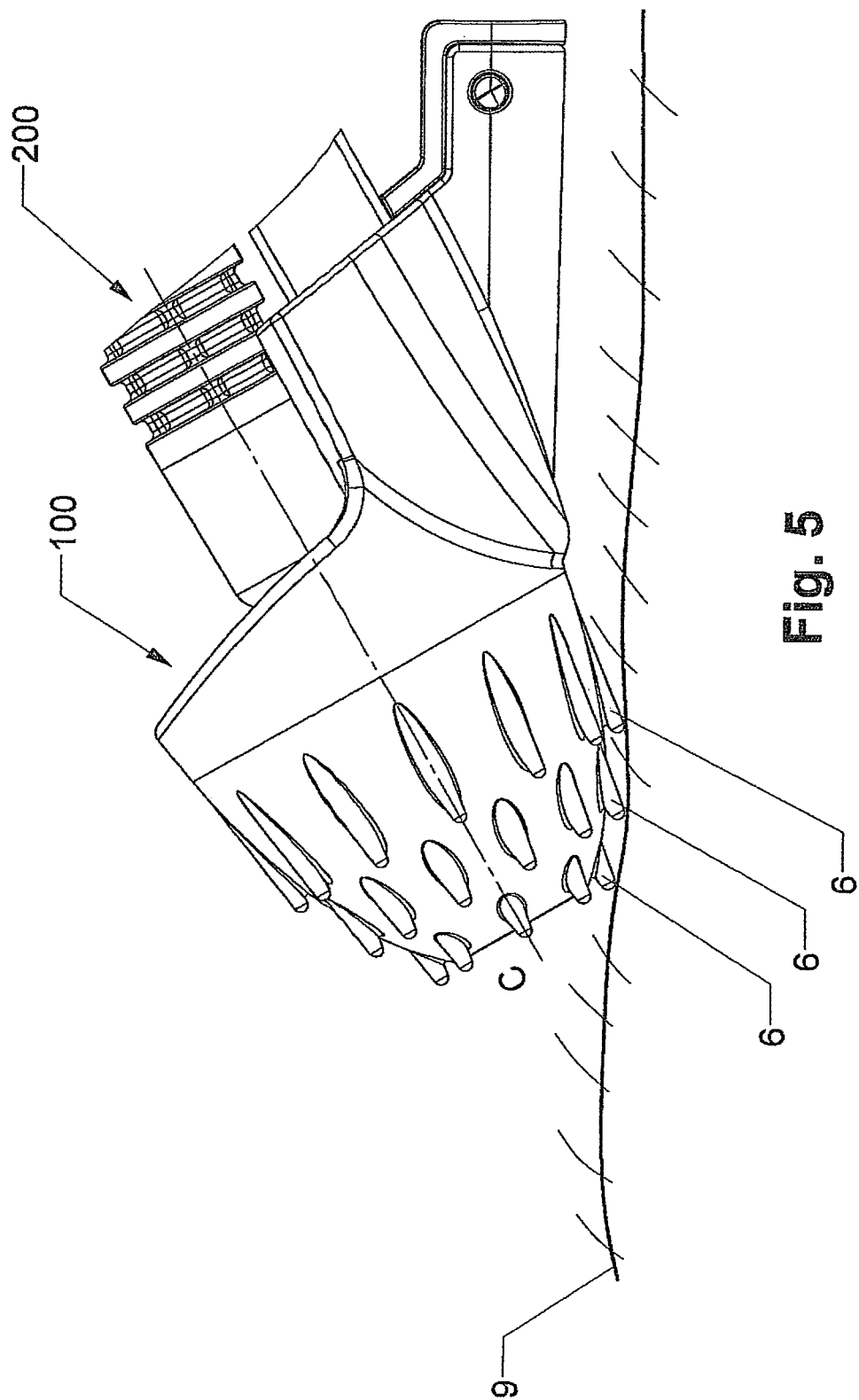

SKIN GRIPPING MEANS, INJECTOR INCLUDING THE SKIN GRIPPING MEANS AND METHOD OF PERFORMING A SUBCUTANEOUS INJECTION

TECHNICAL FIELD

The present invention relates to methods and apparatus for performing subcutaneous injections, and in particular, but not exclusively, to a method and apparatus which allows a subcutaneous injection to be performed with a single handed operation.

BACKGROUND TO THE INVENTION

In order to optimise yield from farmed animals, in particular sheep and cattle, a number of remedies may be injected into the animal by the use of an applicator known as an injector. An example of this type of injector is described in International Publication No. WO2008/143529, the content of which is included herein by reference.

Injection of the animal can be difficult, and a danger exists that the user of the injector may be accidentally jabbed with the needle. Accidents of this type are known as "needle stick". In extreme cases the user may even receive an accidental dose or partial dose of the remedy. This is particularly undesirable, as some of the remedies used with this type of applicator may have significant adverse effects on the health and wellbeing of a human being.

Some injectors of the prior art attempt to reduce the risk of accidental needle stick by covering the needle of the injector with a retractable shroud or "needle guard". The shroud may be spring loaded so that it retracts as the needle is inserted into the animal. The injector described in International Publication No. WO2008/143529 is an example of this type.

Another example of a needle guard of the prior art is shown in FIG. 8 and generally referenced by arrow 300. The needle guard 300 shown in FIG. 8 is intended for use with a powered injector. The guard 300 is provided with a plurality of broad "teeth" 301, which assist in preventing the applicator from sliding on the animal's skin or hide when the injection is administered. The teeth 301 are adapted to reduce sliding on the hide when the needle guard is held substantially orthogonal to the skin.

When using an injector of the prior art to inject an animal with a subcutaneous injection, the operator must use the hand which is not holding the injector to "pinch" a fold of the animal's skin, and then inject the remedy into the subcutis beneath the fold of skin. The proximity of the operator's hand to the injection site contributes substantially to the risk of a needle stick injury.

It would be desirable to create an injector and/or a skin gripping means for use with an injector, which allowed the operator's free hand to be clear of the injection site, even when administering a subcutaneous injection.

The reference to any prior art in the specification is not, and should not be taken as, an acknowledgement or any form of suggestion that the prior art forms part of the common general knowledge in any country.

OBJECT OF THE INVENTION

It is an object of the present invention to provide skin gripping means for use with a suitable injector and/or a needle guard for use with a suitable injector and/or an injector for injecting animals and/or a method of performing a subcutaneous injection which overcomes or ameliorates one or more of the above mentioned problems, or which at least provides a useful choice.

Further objects of the invention may become apparent from the following description, which is given by way of example only.

BRIEF SUMMARY OF THE INVENTION

According to first broad aspect of the present invention there is provided a skin gripping means for use with an injector, an exterior surface of the skin gripping means provided with a plurality of fingers adapted to engage a subject's skin when in use.

Preferably the injector is provided with a needle and the skin gripping means is provided adjacent the needle.

Preferably the injector is a needle free injector provided with an injection orifice, wherein the skin gripping means is provided adjacent the injection orifice.

Preferably the skin gripping means is releasably connectable to the injector.

Preferably the skin gripping means is integral with the injector.

Preferably the skin gripping means comprises a body slidably mounted to the injector.

Preferably the body extends at least partially around a needle of the injector.

Preferably the skin gripping means is adapted for use with a predetermined genus of animal.

Preferably the fingers are sufficiently long to penetrate the coat of the predetermined genus of animal and engage the skin.

Preferably the length and spacing of the fingers is selected for use with cattle.

Preferably the fingers are sufficiently sharp to grip the skin of the predetermined genus of animal, but not sharp enough to pierce the animal's skin when in use.

Preferably the fingers are shaped and dimensioned to grip the skin of the predetermined genus of animal when engaged at a non-orthogonal angle to the skin.

Preferably the angle is between 20° and 45°.

Preferably the angle is substantially 45°.

Preferably the fingers are substantially parallel to each other.

Preferably the fingers have rounded tips.

Preferably the fingers have substantially hemispherical tips.

Preferably all of the tips have substantially the same radius.

Preferably the tips have a radius of approximately 0.6 mm.

Preferably wherein the fingers have a substantially circular or oval transverse cross-section.

Preferably the fingers are substantially conical or pyramidal.

Preferably the fingers are arranged in concentric circles.

Preferably the fingers are arranged into three concentric circles, and any radial line extending from the centre of the concentric circles intersects no more than two of the said fingers.

According to a second broad aspect of the present invention there is provided a needle guard for use with a suitable injector, an exterior surface of the needle guard provided with a plurality of fingers adapted to engage a subject's skin when in use.

Preferably the subject is a non-human.

Preferably the injector is a veterinary injector.

According to a third broad aspect of the invention there is provided a needle guard for use with a suitable injector, the needle guard comprising a hollow body having a first opening at a first end and a second opening at an opposite second end, the body provided with mounting means for mounting the needle guard to the injector such that a needle of the injector protrudes from the first aperture when in use, the body provided with a plurality of fingers extending from an outer surface of the body toward the first end, the fingers being shaped and dimensioned to grip an animal's skin when in use.

Preferably the fingers are shaped and dimensioned to grip an animal's skin when engaged at a non-orthogonal angle to the skin.

Preferably the fingers are shaped and dimensioned to grip an animal's skin when engaged at an angle of between substantially 20° and 45° to the skin.

Preferably the fingers are substantially parallel to each other.

Preferably the fingers have a substantially circular or oval transverse cross-section.

Preferably the needle guard is adapted for use with a predetermined genus of animal.

Preferably the fingers are sufficiently long to penetrate the coat of the predetermined genus of animal and engage the skin.

Preferably the fingers have rounded tips.

Preferably the fingers are sufficiently sharp to grip the skin of the predetermined genus of animal, but not sharp enough to pierce the animal's skin when in use.

Preferably the fingers are substantially conical or pyramidal.

According to a fourth broad aspect of the present invention there is provided a veterinary injector provided with a skin gripping means of the first aspect, or a needle guard of the second or third aspects.

According to a fifth aspect of the present invention there is provided a method of performing a subcutaneous injection comprising the steps of:
 Bringing a skin gripping means of an injector into contact with the skin of a subject;
 Moving the skin gripping means substantially parallel to the skin to thereby form a fold in the skin;
 Moving a needle of the injector into the fold to a suitable position for a subcutaneous injection; and
 Injecting a substance through the needle.

Preferably the method is performed on a non-human.

Preferably the needle guard is provided with a plurality of fingers.

Preferably step i) comprises bringing the skin gripping means into contact with the skin such that a needle of the injector forms an angle of between substantially 20° and 45° with a plane of the skin.

Preferably the injector forms an angle of substantially 45° to the plane of the skin.

Preferably the skin gripping means is a skin gripping means according to the first aspect.

According to a sixth broad aspect of the present invention there is provided a method of performing a subcutaneous injection comprising the steps of:
 Bringing a needle guard of an injector into contact with the skin of a subject;
 Moving the needle guard substantially parallel to the skin to thereby form a fold in the skin;
 Moving a needle of the injector into the fold to a suitable position for a subcutaneous injection; and
 Injecting a substance through the needle.

Preferably the method is performed on a non-human.

Preferably the needle guard is provided with a plurality of fingers.

Preferably the needle guard is a needle guard according to the second or third aspects.

Preferably said step i) comprises bringing the needle guard into contact with the skin such that a needle of the injector forms an angle of substantially 45° with a plane of the skin.

According to a seventh aspect of the invention there is provided a method of performing a subcutaneous injection comprising the steps of:
 Bringing a skin gripping means of an injector into contact with the skin of a subject;
 Moving the skin gripping means substantially parallel to the skin to thereby form a fold in the skin; and
 Injecting a substance into the fold so formed.

Preferably the injector is a needless injector.

According to a further broad aspect of the present invention there is provided a skin gripping means substantially as herein described with reference to the accompanying drawings.

According to a still further broad aspect of the present invention there is provided a needle guard substantially as herein described with reference to the accompanying drawings.

According to a still further broad aspect of the present invention there is provided a method of performing a subcutaneous injection substantially as herein described.

The invention may also be said broadly to consist in the parts, elements and features referred to or indicated in the specification of the application, individually or collectively, in any or all combinations of two or more of said parts, elements or features, and where specific integers are mentioned herein which have known equivalents in the art to which the invention relates, such known equivalents are deemed to be incorporated herein as if individually set forth.

Further aspects of the invention, which should be considered in all its novel aspects, will become apparent from the following description given by way of example of possible embodiments of the invention.

BRIEF DESCRIPTION OF THE FIGURES

FIG. 2 is a side view of the needle guard of FIG. 1.

FIG. 5 is an enlarged side view of the injector and needle guard of FIG. 1 in use engaging an animal's skin prior to performing a subcutaneous injection:

BRIEF DESCRIPTION OF PREFERRED EMBODIMENTS OF THE INVENTION

Figure 1:
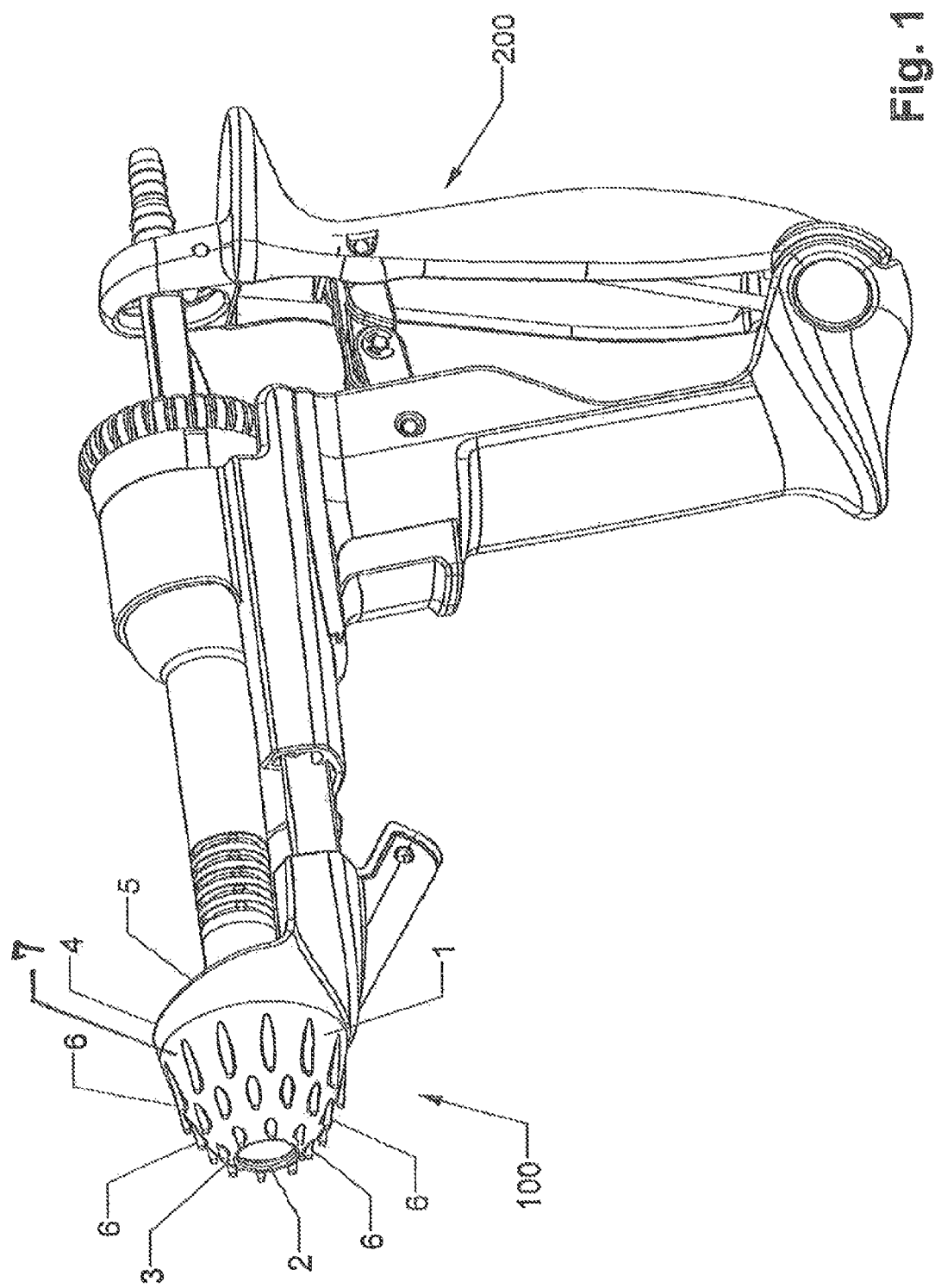
FIG. 1 is a perspective view of an injector provided with a skin gripping means of the present invention configured as a needle guard.

Referring first to FIGS. 1 to 4, a skin gripping means according to one embodiment of the invention is generally referenced by arrow 100. In the embodiment shown the skin gripping means is also a needle guard, and is referred to hereinafter as a needle guard 100, although in other embodiments the skin gripping means may take other forms, as is described below.

The needle guard 100 is releasably connected to an injector, generally referenced by arrow 200. The needle guard 100 shown in FIGS. 1-4 is adapted for use with cattle such as *Bos Indicus* and *Bos Taurus*.

The needle guard 100 comprises a substantially hollow body 1 which has a first aperture 2 therethrough at a first end 3 thereof. The body 1 has a second aperture 4 at a second end 5 which is opposite the first end 3.

The second aperture 4 is preferably larger than the first aperture 2, and the hollow body 1 is preferably smoothly tapered towards the first end 3, thereby forming a substantially frustoconical shape, with the sides of the body being curved in a substantially semi-parabolic fashion.

The hollow body 1 is provided with a plurality of prongs or fingers 6 which extend from an outer surface 7 of the hollow body 1 towards the first end 3 of the hollow body 1. The fingers 6 are provided to grip a subject animal's skin when a subcutaneous injection is being performed, as is described further below. The fingers are intended to grip the skin rather than to pierce, although occasionally the use of the apparatus may result in the skin being pierced.

Figure 4:
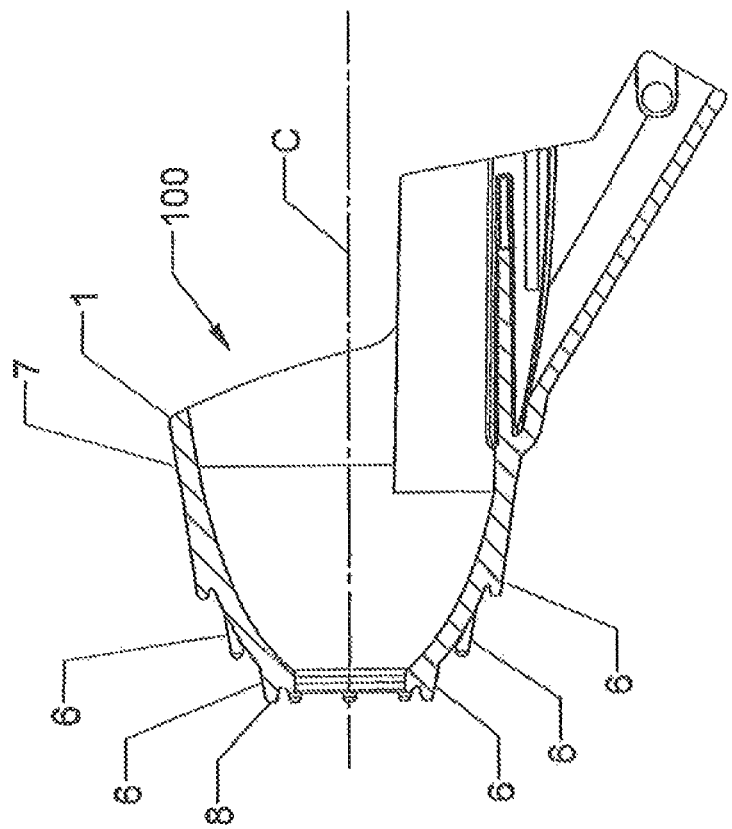
FIG. 4 is a cross section view through line 4-4 in FIG. 3 with the connecting spear removed.
Figure 3:
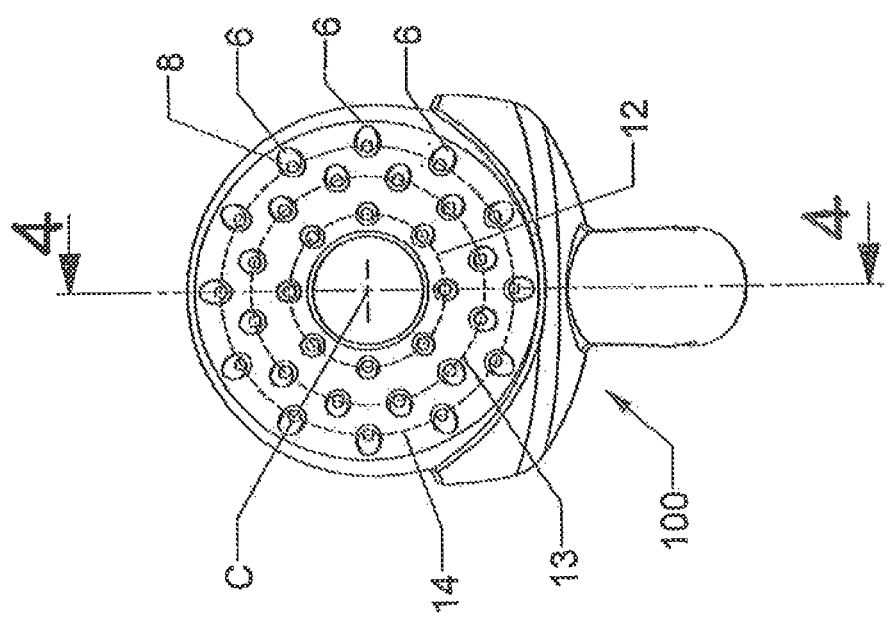
FIG. 3 is a front view of the needle guard of FIG. 1.

Referring in particular to FIGS. 3 and 4, the fingers 6 are preferably elongate and are preferably substantially parallel to one another, and to a central axis C of the hollow body 1, although they may be angled slightly inwardly towards the central axis C, or outwardly away from axis C.

The fingers 6 are preferably sufficiently long and slender to "comb through" the coat of the animal, so that the end 8 of the fingers 6 can engage with the animal's skin. In the preferred embodiment shown the fingers 6 are substantially rigid.

In the preferred embodiment shown the fingers 6 are sufficiently long to extend through the coat and deform the animal's skin. However, it is preferred that the length of the fingers be such that the outer surface 7 of the hollow body 1 comes into contact with the animal's coat and/or skin before the fingers 6 are able to exert excess pressure on the skin.

The ideal number and distribution of the fingers 6 is connected to the sharpness of the ends 8. If relatively sharp ends 8 are used then a higher concentration of fingers 6 is preferred in order to reduce the risk of excess pressure and/or tearing of the skin. However, it is preferred that the ends 8 of the fingers 6 have a convex, rounded profile, which is preferably substantially hemispherical, as best seen in FIG. 4. In a preferred embodiment the ends of each finger having substantially the same radius, for example 0.6 mm in the embodiment shown. In this way fewer fingers may be provided, which allows a greater space between fingers 6. This in turn facilitates penetration of the fingers 6 through the animal's coat. Relatively "open" spacing of the fingers 6 also assists with reducing buildup of dirt and/or hair on the guard, and assists cleaning. For example, in the preferred embodiment shown, the average clear or "relieved" area around each finger is equal to or greater than substantially six times the maximum cross sectional area of the finger, when the fingers are viewed from a front-on perspective (for example as shown in FIG. 3). It is also preferred that the average clear or relieved area around each finger is equal to or greater than substantially 6 times the maximum cross-sectional area when the fingers are viewed from side on (for example as shown in FIG. 2).

In some embodiments (not shown) the fingers 6 may be provided on selected areas of the outer surface 7 only, for example on the right hand side of the outer surface 7 only (not shown). However, it is preferred that substantially the entire portion of the outer surface 7 surrounding the first aperture 2 is provided with fingers 6, so that the needle guard 100 will grip the animal's skin regardless of the angular orientation of the injector 200 about the central axis C.

As best seen in FIG. 4, the fingers 6 are preferably substantially cylindrical or conical in shape, with a substantially circular or oval transverse cross-section. Alternatively, flat sided substantially pyramidal fingers (not shown) may be used, although it is still preferred that these have convex or rounded ends.

Figure 6:
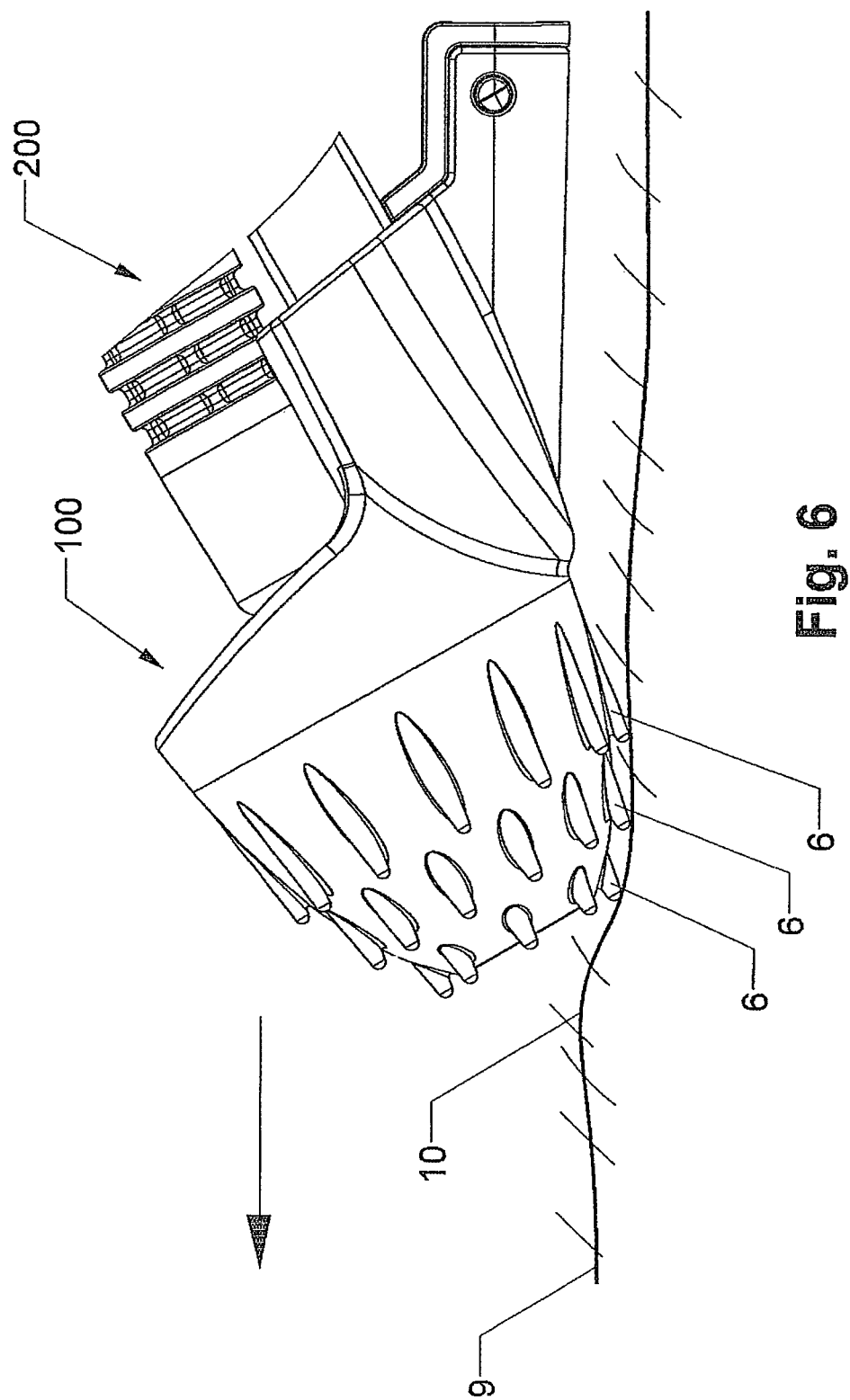
FIG. 6 shows the injector of FIG. 5 beginning to form a fold of skin.
Figure 7:
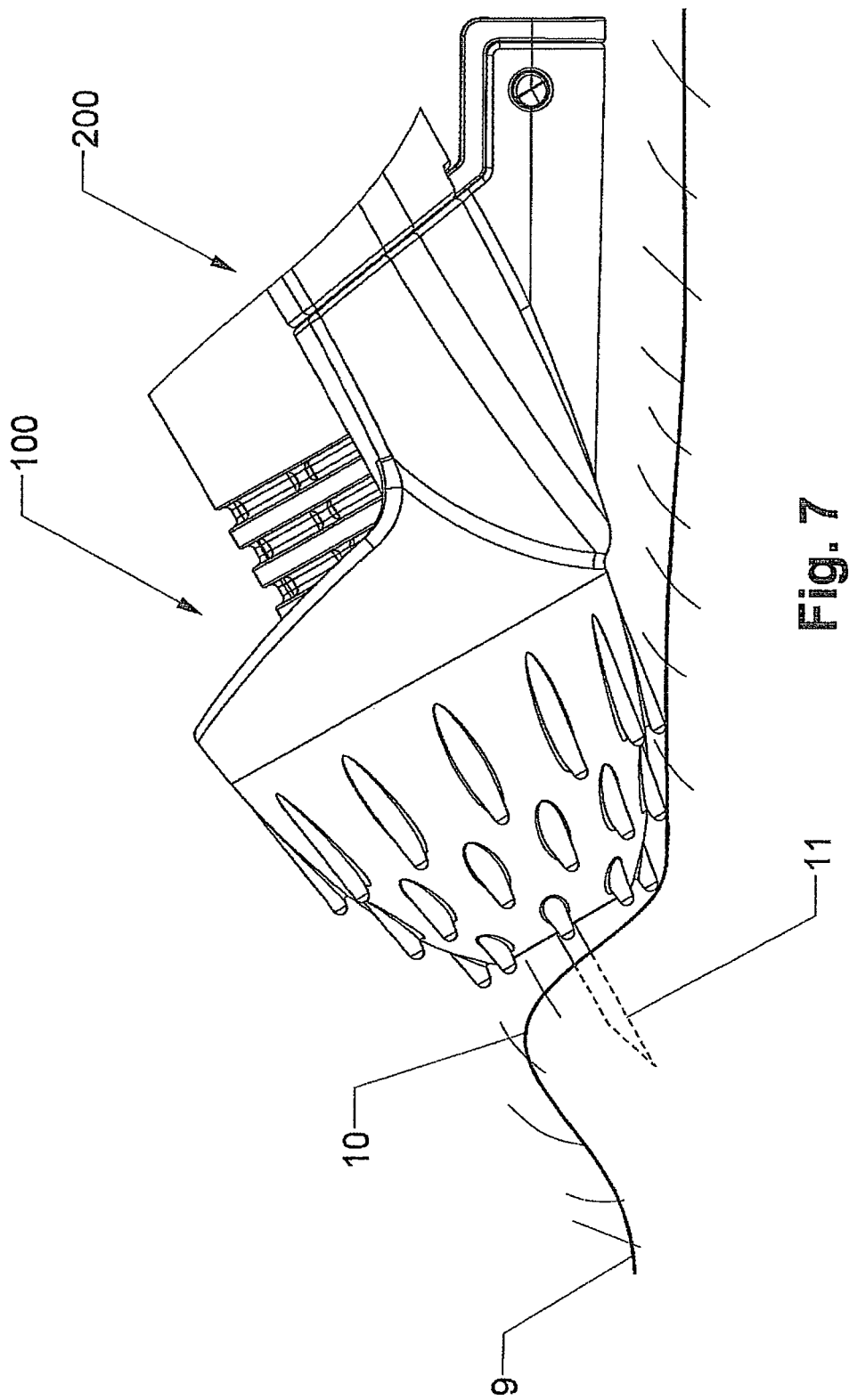
FIG. 7 shows the injector of FIG. 5 performing the subcutaneous injection into the fold of skin.
Figure 8:
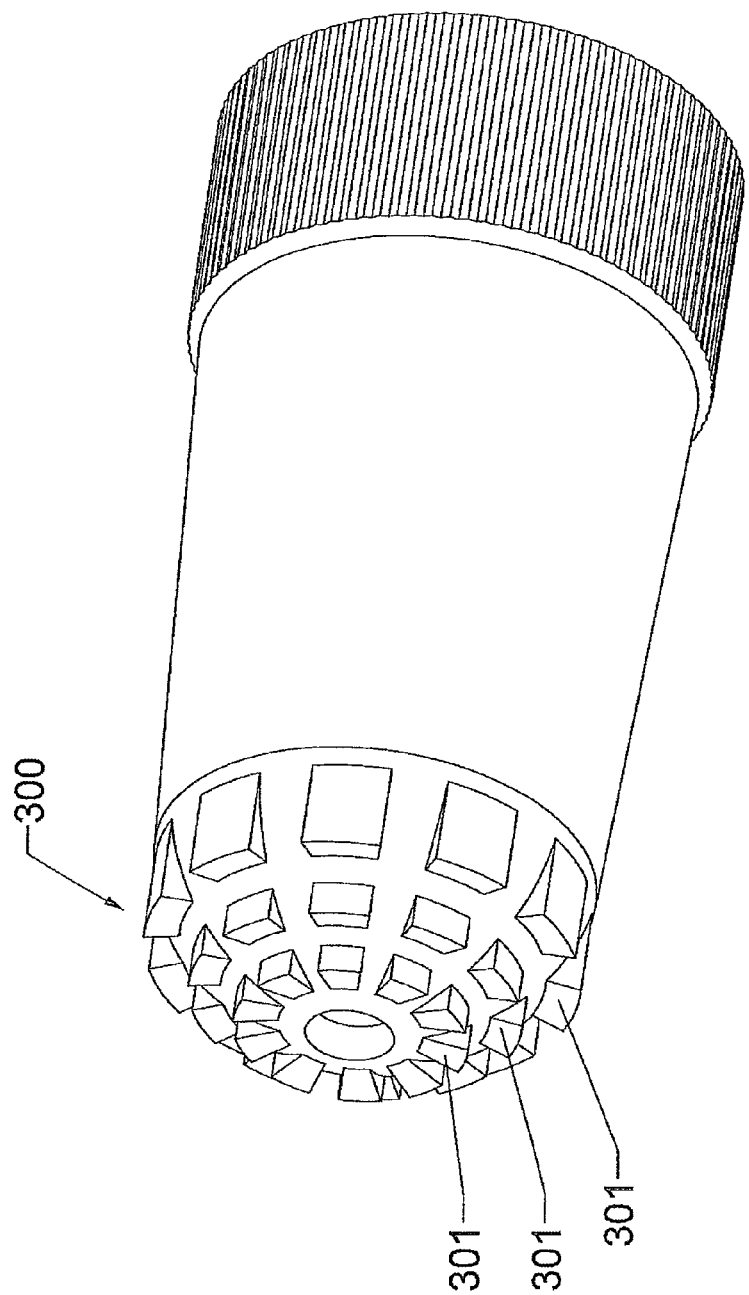
FIG. 8 shows a perspective view of a needle guard of the prior art.

Referring next to FIGS. 5, 6 and 7, a method of using the skin gripping means to perform a subcutaneous injection is described. The needle guard 100 is mounted to a suitable injector 200 (only partially shown in FIGS. 5-7), such as the injector described in International Publication No. WO2008/143529.

As is shown in FIG. 5, the injector is positioned such that the needle guard 100 is pressed onto the subject animal's skin 9 such that the central axis C forms an angle of less than 90°, preferably between 20° and 45°, and more preferably around 45°, to the plane of the skin 9. As is shown in FIG. 6, the needle guard 100 is then moved substantially parallel to the skin 9, while maintaining pressure on the skin 9. The fingers 6 grip the skin 9, and a fold or "tent" 10 of skin 9 begins to be created in front of the needle guard 100. It is preferred that the injector is provided with means to lock the needle guard 100, to ensure that it does not slide back and expose the needle during this process. However, in some embodiments the needle guard may be sufficiently biased towards a position which covers the needle that a separate locking mechanism is not required.

Once a sufficiently large fold 10 has been created, the needle guard 100 can be moved relative to the injector needle 11 so that the needle 11 enters the skin fold 10, as is shown in FIG. 7. The remedy can then be injected through the needle 11 into the area beneath the skin 9, as is normal with a subcutaneous injection. The needle 11 is preferably aligned with axis C.

As can be seen in FIG. 7, the fingers 6 are preferably arranged so as to be substantially parallel to the axis of the injector needle 11 when in use. As can be seen in FIGS. 6 and 7, once the fingers 6 have initially gripped the skin and a fold 10 of skin 9 begins to form, the angle of finger 6 to skin 9 continues to improve with respect to traction, that is, the fingers 6 initially engage the skin 9 at an angle close to 45°, but their grip steadily improves as the fold 10 of skin rises and the angle between the skin 9 and the fingers 6 moves towards 90°. If the fingers 6 were aligned in some other fashion, the initial grip might be improved, but the fingers 6 might lose traction as the fold 10 is formed.

Referring back to FIGS. 1-4, the size of the second aperture 4 is preferably sufficiently large to allow an operator to observe the needle through the aperture 4. In the embodiment shown the second aperture 4 is around 30 mm across. The guard 100 is preferably also made from a substantially transparent material, for example clear polycarbonate, to allow the needle to be viewed through the side wall.

The first aperture 2 is preferably large enough to allow a needle sheath (not shown) to fit inside the aperture 2, so that the injector needle 11 can be changed without the need to remove the guard 100 from the injector 200. In the embodiment shown the first aperture 2 has a diameter of approximately 10 mm. The needle guard shown has a length of around 60 mm, the fingers have a width of around 2 mm and the ends 8 are substantially hemispherical.

Referring in particular to FIG. 3, in a preferred embodiment the fingers 6 are arranged in three rings of fingers 6, having their centres on three substantially concentric notional circles 12, 13, 14. The circles have diameters of 15 mm, 23 mm and 29 mm, and are centred on the axis C. Eight fingers 6 are provided around the inner ring 12, twelve fingers are provided around the intermediate ring 13, and twelve fingers are provided around the outer ring 14. Preferably the length of the fingers increases the further away the fingers are from the first aperture 2.

In the preferred embodiment shown, the fingers are arranged such that any radial line extending from axis C intersects a maximum of two fingers, in order to avoid "shadowing" of the rearward fingers by the forward fingers and thereby ensure that each finger is able to make proper contact with the animal's hide.

The lengths of the fingers in the example shown are as follows:

|  | Radially inward side of finger | Outside of finger |
|---|---|---|
| First circle 12 | 1.6 mm | 3.9 mm |
| Second circle 13 | 1.45 mm | 5.9 mm |
| Third circle 14 | 1.2 mm | 11.04 mm |

As is mentioned above, the example shown in the figures is adapted for use with cattle such as *Bos Indicus* and *Bos Taurus*. However, other embodiments may have finger spacing and length adjusted to be suitable for a different predetermined genus such as sheep.

As is best seen in FIG. 2, the needle guard 100 shown is provided with a barbed spear 15 which is adapted to engage a suitable fitting on an injector in a "clip fit" manner. However, any suitable means of engaging the needle guard 100 with an injector, such as are well known to those skilled in the art, may be used. In other embodiments the needle guard may be integral with the injector.

While the embodiment shown in the figures uses a skin gripping means which also functions as a needle guard, in other embodiments the skin gripping means may not be a needle guard.

In some embodiments (not shown) the body of the skin gripping means may be slideably connected to the injector, but may not extend beyond the tip of the injector needle, even when in an extended position. In other embodiments the body of the skin gripping means may only extend partially around the needle, rather than extending around the needle as shown in the Figures. In yet another embodiment the needle of the injector may be moveable relative to the skin gripping means, rather than the skin gripping means being slidable relative to the needle and the body of the injector, or the injector may be adapted to advance the needle at the same time as the skin gripping means retracts. The skin gripping means may be releasably connectable to the injector, or may be integral with the injector.

Those skilled in the art will appreciate that while the embodiment shown and described herein is suitable for use with cattle, different embodiments of the skin gripping means may be required for use with other animals. Although in the embodiment shown the fingers are arranged so as to grip the animal's skin to provide traction, in other possible embodiments the fingers 6 may engage the animal's coat, or a combination of skin and coat.

Those skilled in the art will also appreciate that the present invention provides an apparatus and method which allows an operator to perform a subcutaneous injection with a one-handed operation, and without positioning his or her hand near the injection site. This dramatically decreases the chances of a needle stick incident occurring.

While the invention has been described above with reference to embodiments in which the injection is performed with a needle, those skilled in the art will appreciate that in some alternative embodiments the injector may be of the "needle free" type. This type of injector is provided with a small diameter injection orifice through which the remedy is forced under pressure, creating a high pressure jet which pierces the skin.

Where in the foregoing description, reference has been made to specific components or integers of the invention having known equivalents, then such equivalents are herein incorporated as if individually set forth.

Although this invention has been described by way of example and with reference to possible embodiments thereof, it is to be understood that modifications or improvements may be made thereto without departing from the spirit or scope of the appended claims.

Unless the context clearly requires otherwise, throughout the description and the claims the words "comprise," "comprising," and the like are to be construed in an inclusive sense as opposed to an exclusive or exhaustive sense, that is to say, in the sense of "including, but not limited to."

The invention claimed is:

1. A method of performing a subcutaneous injection comprising the steps of:
   i. bringing a skin-gripping means of an injector into contact with the skin of a subject at an angle of between 20° and 45° to the skin, without breaking the skin, the skin-gripping means having an exterior surface with a curved portion which has a semi-parabolic profile, the skin-gripping means including a plurality of slender fingers which extend from the curved portion of the exterior surface, each of the plurality of slender fingers having a tip for gripping the subject's skin when engaged at an angle of between 20° and 45° to the skin, in use;
   ii. moving the skin-gripping means, while engaged with the subject's skin at an angle between 20° and 45° to the skin and without breaking the skin, substantially parallel to the skin to thereby form a fold in the skin; and
   iii. injecting a substance into said fold.

2. The method of claim 1, wherein the skin-gripping means comprises a body slidably mounted to the injector.

3. The method of claim 2, wherein the body extends at least partially around a needle of the injector when in use.

4. The method of claim 1, wherein the plurality of slender fingers are substantially parallel to each other.

5. The method of claim 1, wherein each of the plurality of slender fingers has a hemispherical tip.

6. The method of claim 5, wherein each tip has a radius of approximately 0.6 mm.

7. The method of claim 1, wherein the plurality of slender fingers are arranged in concentric circles.

8. The method of claim 7, wherein the plurality of slender fingers are arranged into three concentric circles, and any radial line extending from a center of the three concentric circles intersects no more than two of the plurality of slender fingers.

* * * * *